United States Patent [19]

van Paassen et al.

[11] Patent Number: 4,645,627

[45] Date of Patent: Feb. 24, 1987

[54] SALTS OF ACID ETHER SULPHATES AND A PROCESS FOR THE PREPARATION OF THESE SALTS

[75] Inventors: Nicolaas A. I. van Paassen; Jacobus G. Verschuur, both of Bodegraven, Netherlands

[73] Assignee: Stamicarbon B.V., Geleen, Netherlands

[21] Appl. No.: 713,649

[22] Filed: Mar. 19, 1985

Related U.S. Application Data

[63] Continuation of Ser. No. 503,395, Jun. 10, 1983, abandoned.

[30] Foreign Application Priority Data

Jun. 12, 1982 [NL] Netherlands ............ 8202398

[51] Int. Cl.$^4$ ............................................. C07C 87/00
[52] U.S. Cl. ................ 260/501.21; 252/355; 252/545; 252/551
[58] Field of Search ............ 260/501.21; 252/355, 252/545, 551

[56] References Cited

U.S. PATENT DOCUMENTS

| | | | |
|---|---|---|---|
| 2,052,027 | 8/1936 | Harris | 252/355 |
| 2,126,054 | 8/1938 | Steik et al. | 252/355 |
| 2,303,348 | 12/1942 | Freeman et al. | 252/355 |
| 2,686,201 | 8/1954 | Keenan | 252/355 |
| 4,235,898 | 11/1980 | Watanabe et al. | 252/545 |

FOREIGN PATENT DOCUMENTS 891631  3/1962  United Kingdom ........... 260/501.21

OTHER PUBLICATIONS

Soap/Cosmetics/Chemical Specialties, Jan. 1977, The Application of Primary Alcohol Ethoxysulfates in Laundry Detergents, pp. 39–46.
Fette, Seifen, Anstrichmittel, 80 Jahrgang, No. 10, 1978, p. 394, Chemical Abstracts, vol. 96, 1982, p. 114.

*Primary Examiner*—Glennon H. Hollrah
*Assistant Examiner*—Raymond Covington
*Attorney, Agent, or Firm*—Cushman, Darby & Cushman

[57] ABSTRACT

Virtually odor-free, non-gelling, water-dilutable and acceptably colored salts of acid ether sulfates, being liquid under normal temperature and pressure conditions, are obtained by neutralizing acid sulfates of the general formula $R(OCH_2CH_2)_nOSO_2OH$ wherein n has an average value between 1 to 6 and R is an oleyl or alkyl group of 8 to 16 carbon atoms which acid sulfate has been neutralized with triisopropanolamine. Such salts are suitable for half care products and for anhydrous insecticide preparations.

5 Claims, No Drawings

SALTS OF ACID ETHER SULPHATES AND A PROCESS FOR THE PREPARATION OF THESE SALTS

This is a continuation of application Ser. No. 503,395, filed June 10, 1983, now abandoned.

BACKGROUND AND SUMMARY OF THE INVENTION

This invention relates to salts of acid ether sulphates which are in the liquid state under normal temperature and pressure conditions and to a method for preparing these salts.

Salts having very good surface activity can be prepared by neutralization of acid sulphates of the general formula $R(OCH_2CH_2)_nOSO_2OH$, where n represents a number having an average value of 2 to 3 and R is an alkyl group with 8 to 16 carbon atoms with an amine from the group of diethylamine, butylethanolamine, and isopropylamine or mixtures thereof as disclosed in British Pat. No. 891,631.

Also known are sodium salts of acid sulfates corresponding to the formula $C_{12}H_{25}(OCH_2CH_2)_nOSO_2OH$. Neutralization of the acid sulfate with sodium hydroxide yields a neutral salt having a very good surface-active activity. As the n value in this formula increases the consistency undergoes a gradual change from a solid through a paste like state to a liquid state. For instance with sodium lauryl sulfate where n=o the salt is a solid. Surface activity does not increase substantially for n>3 and for higher n values the cost of the product increases. Therefore in practice n values are about 3 or less. With an n value in excess of 3 these sodium salts are still pasty.

The salts of the British patent compared with the above-described sodium salts do exhibit some advantages. For instance the non-sodium salts described in British Pat. No. 891,631 have the advantage that they do not have a pasty consistency under normal temperature and pressure conditions but are liquid. This cuts down transport costs and is also important for water-free applications of said salts. Most disadvantageously however these known salts have poor color characteristics and are malodorous thereby in reality rendering these salts less suitable for various applications despite contrary statements in text references. In addition, it is difficult to dilute them with water because gel formation takes place.

In addition, the results from other neutralization reactions using triethyanolamine are very discouraging since the thus formed salts are reportedly very pasty in an anhydrous condition even for n values of 2 to 3. Indeed, use of even monoethanolamine and/or ethylethanolamine as the basic component in the neutralization reaction also yields a pasty product.

Surprisingly, it has now been found that in accordance with the present invention that the neutralization of various acid ether sulphates with tri-isopropanolamine yields salts that not only have a suitable odor and color but also are liquid under normal temperature and pressure conditions. Furthermore these novel salts can be dissolved in water without the occurence of gel formation.

DESCRIPTION OF THE PRESENT INVENTION

The salts according to the invention are salts of acid sulphates of the general formula $R(OCH_2CH_2)_nOSO_2OH$, wherein n represents a number having an average value of 1 to 6 and R an oleyl group or an alkyl group with 8 to 16 carbon atoms, with tri-isopropanolamine. Suitable alkyl groups include for instance, aliphatic hydrocarbon groups, such as, octyl or nonyl groups.

According to the invention particularly suitable are the salts where n represents a number having an average value of 1.5 to 3.5, for instance the salt in which R represents a lauryl group and n an average value of 2.

The acid sulphates of the above-mentioned general formula can be obtained in a known way by condensing the corresponding alcohol (ROH) with epoxyethane in an amount corresponding with the desired average number of ethoxy groups and sulphating the thus formed reaction product. Starting from a mixture of alcohols, for instance technical grade lauryl alcohol, a corresponding mixture of the acid sulphates is obtained which sulfates may then be converted to the corresponding mixture of salts according to the present invention using tri-isopropanolamine. Suitable condensation products for the sulfation reaction include, for example, Synperonic from I.C.I. Other suitable condensation products will now be apparent to those skilled in the art in view of the present disclosure.

The di- and/or tri-ethoxy compound, for instance, may be isolated from the reaction product obtained by sulphating the condensation product formed from the alcohol or the mixture of alcohols with epoxyethane. The di and/or tri ethoxy sulfated compound may then be employed as the acid reactant in the neutralization reaction process with tri-isopropanolamine.

The neutralization of the acid sulphate with tri-isopropanolamine may, for instance, be accomplished by gradually adding the melted amine (melting point 58° C.) to the acid sulphate whilst stirring. The means whereby the tri-isopropanolamine is added to the acid sulfate is not critical and may, for instance, include adding the material as a melt below the surface of the acid sulfate in the process vessel. The neutralization can be effected using reflux cooling or can be conducted under pressure in a closed system. Preferably, the temperature is then between about 35° C. to about 45° C. since this makes stirring of the reaction mixture easier than at normal ambient temperatures.

In the present process, the amount of tir-isopropanolamine is selected to yield an aqueous solution of the end product having a pH of about 5.5. The pH may range from about 4.2 to about 6. This neutralization requires an amount of amine that is greater than the stoichiometric amount, since the tri-isopropanolamine is not a strong base, the acid sulphate has a strongly acid character, and acid impurities are present.

The salts according to the present invention are suitable for various purposes, for instance, such as a hair washing agent or as an emulsifier in anhydrous systems such as anhydrous insecticide preparations.

The present invention will be elucidated by the following non-limiting examples. The salts obtained according to all the following examples are practically odorless and have a light-yellow to yellow color.

EXAMPLE I

Technical-grade octyl alcohol is condensed with 3.3 moles epoxyethane per mole alcohol. While being stirred, the thus obtained condensation product (345 g) is sulphated with 150 g $HSO_3Cl$. The $HSO_3Cl$ is gradually added to the condensation product over a period of about 30 minutes. During this time the temperature increases to about 33° C. The resultant reaction mixture is subsequently stirred while being kept at 40° C. for 40 minutes. 451 grams acid sulphate is obtained, the Epton value of which is calculated to be 2.77 milligram equivalents per gram.

A 448.5 grams sample of the acid sulphate is then recovered and neutralized with 267 grams of tri-isopropanolamine (hereinafter referred to as tipa) at 40° C. This neutralization yielded 713 grams of the desired salt. The salt had an Epton value of 1.58 mgeq/g. 4 grams of acetic acid (having a buffering effect so that the pH is stabilized) was added to the product and the product was diluted to a 10 weight percent concentrated solution. The solution, of course, was prepared by diluting with water. The pH of this diluted solution was 5.1.

EXAMPLE II

Over a period of 30 minutes and while the condensation reactant is being stirred, 120 grams of $HSO_3Cl$ is gradually added to 348 grams of a condensation product that is commercially available under the name Synperonic (3 moles epoxyethane per mole of a mixture of $C_{11}$ to $C_{13}$ alcohols, available under the name Synprol). The temperature increases to 35° C.

The resulting mixture is subsequently kept at 38° C. for 40 minutes. During this time the reaction mixture is stirred and has nitrogen gas passed through it. 433.5 grams of acid sulphate is obtained. This acid sulfate has a calculated Epton value of 2.31 mgeq/g.

At a temperature of 40° C., 404.5 grams of the acid sulphate is neutralized with 211.5 grams tipa. 616 grams of salt is obtained, the Epton value of which is calculated to be 1.43 mgeq/g. After dilution with water to a concentration of 10 weight percent, the salt has a pH of 5.2.

EXAMPLE III

In 3.5 hours' time 1489 grams of $HSO_3Cl$ is gradually added to 2565 grams of the product of condensation of technical-grade lauryl alcohol with 2 moles epoxyethane per mole alcohol. Meanwhile, the condensation product is being stirred. The temperature increases to about 35° C. While being stirred, and while nitrogen is passed through it, the thus obtained mixture is subsequently kept at 40° C. for 45 minutes. 3329 grams of acid sulphate is obtained, the Epton value of which is calculated to be 2.7 mgeq/g.

3275 grams of the acid sulphate obtained is neutralized with 1885 grams tipa at about 40° C. The yield is 5160 grams, with an Epton value of 1.61 mgeq/g. The pH of the water-diluted salt (10 weight percent) is 5.55.

EXAMPLE IV

Over a period of 35 minutes 118 grams of $HSO_3Cl$ is gradually added to 392 grams of the product of condensation of technical-grade oleyl alcohol with 3.2 mmoles epoxyethan per mmole alcohol. Meanwhile, the condensation product is being stirred. The temperature increases to about 35° C. The mixture obtained is stirred and nitrogen is passed through it while being maintained at 40° C. for 30 minutes. 486 grams of acid sulphate is obtained, the Epton value of which is calculated to be 2.02 mgeq/g.

406 grams of the acid sulphate product is neturalized with 207 grams of tipa at 35° to 40° C. 613 grams of salt are obtained. The Epton value of the salt is calculated to be 1.25 grams mgeq/g. The pH of the water-diluted salt (10 weight percent) is 5.2.

While the present invention has now been described in terms of the presently considered preferred embodiments, it should be recognized that such descriptions are illustrative and not intended to restrict the scope of the present invention set forth in the following claims.

What we claim is:

1. Water-dilutable and non-malodorous acid ether sulphate salts obtained by neutralizing acid sulfates having the formula $R(OCH_2CH_2)_nOSO_2OH$, wherein n represents a number having an average value of 1 to 6 and R is an oleyl group or an alkyl group having 8 to 16 carbon atoms, with tri-isopropanolamine.

2. Salts according to claim 1, where n has an average value of 1.5 to 3.5.

3. Salts according to claim 1, wherein said acid sulfate formula R represents a lauryl group and n has an average value of 2.

4. Salts according to claim 1, wherein R in said formula represents an oleyl group.

5. Process for preparing non-gelling water-dilutable and non-malodorous salts of acid ether sulfates comprising neutralizing an acid ether sulfate of the formula $$R(OCH_2CH_2)_nOSO_2OH,$$

wherein n re-presents a number having an average value of 1 to 6 and R is an oleyl group or an alkyl group having 8 to 16 carbon atoms, with triisopropanolamine to thereby yield acid ether sulfate salts as an end product.

* * * * *